United States Patent
Xiao et al.

(10) Patent No.: US 11,524,041 B2
(45) Date of Patent: *Dec. 13, 2022

(54) GINKGO DITERPENE LACTONE COMPOSITION

(71) Applicant: Jiangsu Kanion Pharmaceutical Co., Ltd., Jiangsu (CN)

(72) Inventors: Wei Xiao, Jiangsu (CN); Enli Zhou, Jiangsu (CN); Zeyu Cao, Jiangsu (CN); Xiujuan Chang, Jiangsu (CN); Xiaodong Kang, Jiangsu (CN); Yongxiang Wang, Jiangsu (CN); Hanfei Hu, Jiangsu (CN); Yun Wu, Jiangsu (CN); Zhenzhong Wang, Jiangsu (CN); Chenfeng Zhang, Jiangsu (CN)

(73) Assignee: JIANGSU KANION PHARMACEUTICAL CO., LTD, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/771,824

(22) PCT Filed: Nov. 13, 2018

(86) PCT No.: PCT/CN2018/115167
§ 371 (c)(1),
(2) Date: Jun. 11, 2020

(87) PCT Pub. No.: WO2019/128499
PCT Pub. Date: Jul. 4, 2019

(65) Prior Publication Data
US 2021/0196773 A1 Jul. 1, 2021

(30) Foreign Application Priority Data
Dec. 29, 2017 (CN) .......................... 201711475539.2

(51) Int. Cl.
| | |
|---|---|
| A61K 36/16 | (2006.01) |
| A61P 39/06 | (2006.01) |
| A61P 25/24 | (2006.01) |
| A61K 9/00 | (2006.01) |
| A61K 31/365 | (2006.01) |

(52) U.S. Cl.
CPC ............ *A61K 36/16* (2013.01); *A61K 9/0019* (2013.01); *A61K 31/365* (2013.01); *A61P 25/24* (2018.01); *A61P 39/06* (2018.01)

(58) Field of Classification Search
CPC .......... A61K 36/16; A61K 25/24; A61P 39/06
See application file for complete search history.

(56) References Cited

FOREIGN PATENT DOCUMENTS

| CN | 1424031 A | 6/2003 |
|---|---|---|
| CN | 1557296 A | 12/2004 |
| CN | 1686317 A | 10/2005 |
| CN | 1977840 A | 6/2007 |
| CN | 105853479 A | 8/2016 |
| CN | 106377517 A | 2/2017 |
| CN | 104914174 B | 7/2017 |
| CN | 107929283 A | 4/2018 |

OTHER PUBLICATIONS

Omar Ginkgolides and neuroprotective effect (2013).*
Wang et al. (Acta Pharmacologica Sinica (2010) 31: 649-664).*
Ginkgo Clinical overview (2002).*
Extended European Search Report dated Oct. 23, 2020 in EP Application No. 18894739.4.
Zihong et al., "GC-MS-based metabolomic study on the antidepressant-like effects of diterpene ginkgolides in mouse hippocampus," Behavioural Brain Research, vol. 314, pp. 116-124 (2016).
Shuwei et al., "Transpost of ginkgolides with different lipophilicities based on an hCMEC/D3 cell monolayer as a blood-brain barrier cell model," Life Sciences, vol. 114, pp. 93-101 (2014).
Shao et al., "Pharmacokinetics of ginkgolides A, B and K after single and multiple intravenous infusions and their interactions with midazolam in healthy Chinese male subjects," Eur. J. Clin. Pharmacol., vol. 73, pp. 537-546 (2017).
Wu et al., "Qualitative and quantitative evaluation of ginkgo terpene lactone raw material by HPLC/Q-TOF MS combined with HPLC-DAD-ELSD," Analytical Methods, vol. 7, pp. 667-674 (2015).

(Continued)

*Primary Examiner* — Shirley V Gembeh

(74) *Attorney, Agent, or Firm* — Panitch Schwarze Belisario & Nadel LLP

(57) ABSTRACT

A *Ginkgo* diterpene lactone composition is provided. The composition has the effect of improving a depressive state. The composition can prolong a tail flick interval time and a swimming interval time of a mouse to different degrees and can also increase the frequency of escaping from electric shock to different degrees. The additional addition of a certain amount of ginkgolide C, ginkgolide J, and ginkgolide L greatly enhances the effect of improving the depressive state. It is further proved through experiments that after the provision of the *Ginkgo* diterpene lactone composition, indexes, such as SOD, MDA, GSH, and TAC, can be improved to different degrees. For example, after the addition of a certain amount of ginkgolide C, ginkgolide J, and ginkgolide L, the improving effect gets more obvious, the oxidative stress level can be better improved, and the oxidative damage can be relieved.

10 Claims, No Drawings

(56) References Cited

OTHER PUBLICATIONS

Int'l Search Report dated Feb. 14, 2019 in Int'l Application No. PCT/CN2018/115167.
First Search Report dated Dec. 24, 2018 in CN Application No. 201711475539.2.
Office Action dated Jan. 2, 2019 in CN Application No. 201711475539.2.
Office Action dated Mar. 1, 2019 in CN Application No. 201711475539.2.
Supplementary Search Report dated Mar. 18, 2019 in CN Application No. 201711475539.2.
Xu et al., "Antagonistic effect of ginkgolide homologues on PAF-induced platelet aggregation and neuroprotective effect," China Journal of Chinese Materia Medica, vol. 42, No. 24, pp. 4716-4721 (2017) (First Page English Abstract).
Zhong et al., "Protection of Diterpene Ginkgolides Meglumine Injection on acute injury of ischemic stroke in rats," Drug Evaluation Research, vol. 40, No. 6, pp. 752-758 (2017) (First Page English Abstract).
Desion of Grant dated Nov. 2, 2021 in Japanese Patent Application No. 2020-536587.
Office Action dated Jun. 28, 2022 in KR Application No. 1020207019561 (English Translation Only).

\* cited by examiner

GINKGO DITERPENE LACTONE COMPOSITION

CROSS-REFERENCE TO RELATED APPLICATIONS

This application is a Section 371 of International Application No. PCT/CN2018/115167, filed Nov. 13, 2018, which was published in the Chinese language on Jul. 4, 2019, under International Publication No. WO 2019/128499 A1, which claims priority under 35 U.S.C. § 119(b) to Chinese Application No. 201711475539.2, filed Dec. 29, 2017, the disclosures of each of which are incorporated herein by reference in their entireties.

TECHNICAL FIELD

The present invention belongs to the technical field of medicine and in particular to a *Ginkgo* diterpene lactone composition.

BACKGROUND

*Ginkgo* tree is also known as maidenhair tree. It is also called Yajiao tree or Gongsun tree in ancient times. It is one of the oldest tree species in the world and its resources are most widely distributed in China, accounting for more than 70% of the world total. *Ginkgo* has been used medicinally for 600 years. *Ginkgo biloba* leaves have a wide range of biological activities and contain a variety of chemical components, including flavonoids, terpenes, polyphenols, phenylpropanoids, organic acids, sugars, fatty acids, lipids, inorganic salts and amino acids. Modern pharmacological studies have proven that *Ginkgo biloba* extract has antioxidant and anti-aging effects and is also capable of lowering blood pressure, promoting blood circulation, and improving brain function.

Ginkgolides are terpenoids and are known as terpene lactones. In 1967, Professor Nakanishi Koji of Columbia University in the United States first reported four diterpene lactones with special structures, namely Ginkgolides A, B, C and M (GA, GB, GC, and GM). Ginkgolide J (GJ) was isolated in 1987, and Ginkgolides K and L (GK and GL) were later discovered. Ginkgolides are unique and important components of *Ginkgo biloba*, with specific anti-PAF (Platelet Activating Factor) activity. They are natural strong PAF antagonists (PAF is an endogenous phospholipid produced by platelets and a variety of inflammatory tissues. It is the most effective platelet aggregation inducer found to date). These PAF antagonists have antioxidant, anti-inflammatory, anti-platelet aggregation, antiapoptosis, anti-cell death and angiectatic pharmacological effects and also can protect nervous centralis and ischemic tissue. They have unique advantages especially in the treatment of ischemic stroke.

CN1424031A reports a ginkgolide preparation, containing 30-40% of GA, 50-65% of GB, and 0.5-5% of GK. Based on the theory of traditional Chinese medicine, traditional Chinese medicine emphasizes the synergistic effect of multiple ingredients. Based on this, the inventors found that when the composition contains GC, GJ, and GL, it will increase the pharmacological effects of the ginkgolide composition in some way.

In view of this, the present invention is intended to find a composition with higher pharmacological activity on the basis of the synergy effect between the ginkgolide monomers.

The present invention provides a *Ginkgo* diterpene lactone composition, comprising, by weight: 32-36 parts of GA, 55-58 parts of GB, 2.2-3.4 parts of GK, wherein, the composition further comprises GC, GJ, and GL, and the total content of GC, GJ and GL is above 2.6 parts. Preferably, the content of each of GC, GJ and GL is not less than 0.5 part.

Preferably, the total content of GC, GJ and GL is 10.8 parts or less.

Preferably, the total content of GC, GJ and GL is between 2.6-10.8 parts.

Preferably, the total content of GC, GJ and GL is between 3.0-6.0 parts.

Preferably, the total content of GC, GJ and GL is between 4.6 parts.

The present invention provides a *Ginkgo* diterpene lactone composition, comprising, by weight: 32-34% of GA, 56-58% of GB, and 2.4-3.4% of GK, wherein the composition further comprises GC, GJ and GL, and the total content of GC, GJ and GL is above 2.6%. Preferably, the content of each of GC, GJ and GL is not less than 0.5%.

Preferably, the total content of GC, GJ and GL is between 2.6% and 10.8%.

Preferably, the total content of GC, GJ and GL is between 3.0% and 6.0%.

Preferably, the total content of GC, GJ and GL is 4.6%.

Preferably, the composition does not comprise bilobalides.

The present invention further provides a *Ginkgo* diterpene lactone preparation containing the above composition, wherein the preparation further comprises pharmaceutically acceptable excipients.

The present invention further provides a *Ginkgo* diterpene lactone injection containing the above composition.

Specifically, the injection is in a dose of 1 ml or 5 ml or 10 ml and contains 5±0.5 mg or 25±0.5 mg or 50±0.5 mg of the *Ginkgo* diterpene lactone composition respectively. Further, the injection further contains meglumine and sodium chloride, and the weight ratio of the *Ginkgo* diterpene lactone composition to meglumine to sodium chloride is (2-8): (2-8): (4-12).

The present invention further provides an application of the above composition in the preparation of an antidepressant drug.

The present invention further provides an application of the above composition in the preparation of a drug for preventing and/or treating cardiovascular and cerebrovascular diseases.

The present invention further provides an application of the above composition in the preparation of a drug for ameliorating oxidative stress.

The wording "application" refers to administering the above-mentioned extract to a subject having a corresponding disease or a pre-disposition to the disease, with the purpose of conferring a therapeutic effect, such as curing, alleviating, changing, influencing, improving or preventing the disease, its symptoms, or its predisposition. Those skilled in the art can easily determine the specific effective dose according to the type of disease to be treated, the route of administration, and the use of excipients, and the dose may vary due to the concurrent use of other drugs.

The present invention utilizes a mouse model to confirm that the *Ginkgo* diterpene lactone composition can extend the tail flick interval and the swimming interval to varying degrees, and also can increase the number of escapes from electric shock to varying degrees; moreover, due to further addition of a certain amount of GC, GJ and GL, the effect of the composition in improving the depression state is greatly improved. In addition, through experiments, the present invention also confirms that after the administration of the *Ginkgo* diterpene lactone composition, SOD, MDA, GSH, and TAC and other indicators can be improved to varying degrees; especially after the addition of a certain amount of GC, GJ, and GL, these improvements are more obvious; the level of oxidative stress can be better improved and the oxidative damage can be relieved.

The wording "above" in the present invention includes the number, for example, above 2.6, including 2.6; and for another example, above 2.6%, including 2.6%.

DETAILED DESCRIPTION OF EMBODIMENTS

The present invention will be described below in more detail through specific embodiments, so as to better understand the solution of the present invention and the advantages of its various aspects. However, the content of the specific embodiments described below is for illustrative purposes only, and should not be construed as limiting the present invention.

It should be noted that if the specific conditions are not specified, they are performed according to the conventional conditions or the conditions recommended by the manufacturer. If the manufacturers of the APIs or excipients used, and of the reagents or instruments used are not specified, they are all regular products which can be commercially available. Unless stated otherwise, all percentages, ratios, proportions or parts are by weight.

Unless otherwise defined, all technical terms and scientific wordings used herein have the same meaning as those familiar to those skilled in the art. In addition, any methods and materials similar or equal to the content described can be applied to the present invention.

Example 1 Anti-Depression Effect of the *Ginkgo* Diterpene Lactone Composition 1. Materials Animals: SPF male SD rats, weighing 200-220 g; SPF male Kunming rats, weighing 20-24 g, provided by Qinglongshan Animal Breeding Farm, Jiangning District, Nanjing, with a certificate number of SCXK (Jiangsu) 2016-0008.

Test drugs: Each *Ginkgo* diterpene lactone compound is a commercially available standard product, and the gingko diterpene lactone composition groups A-K with different ratios of components were formulated according to the ratios described in the table below, and then dissolved with 0.5% meglumine and 0.15% citric acid to prepare experimental solutions. The positive drug was imipramine hydrochloride tablets (provided by Shanghai Jiufu Pharmaceutical Co., Ltd., 25 mg/tablet), which were formulated into 12.5 mg/mL and 5 mg/mL solutions.

The ratios of components in the *Ginkgo* diterpene lactone composition

| Group | Group name | GA | GB | GK | GC | GJ | GL |
|---|---|---|---|---|---|---|---|
| A | Example 1 | 34.1 | 57.9 | 3.4 | 3.6 | 0.5 | 0.5 |
| B | Example 2 | 33.0 | 57.6 | 2.4 | 3.2 | 2.4 | 1.4 |
| C | Example 3 | 32.9 | 56.1 | 3.0 | 3.8 | 3.5 | 0.7 |
| D | Comparison example 1 | 37.2 | 58.3 | 4.5 | 0 | 0 | 0 |
| E | Comparison example 2 | 33.2 | 56.1 | 2.5 | 4.6 | 0 | 0 |
| F | Comparison example 3 | 33.2 | 56.1 | 2.5 | 0 | 4.6 | 0 |
| G | Comparison example 4 | 33.2 | 56.1 | 2.5 | 0 | 0 | 4.6 |
| H | Comparison example 5 | 36.6 | 57.4 | 4.8 | 0.4 | 0.4 | 0.4 |
| I | Comparison example 6 | 34 | 58 | 3.4 | 3.1 | 1.5 | 0 |
| J | Comparison example 7 | 34 | 58 | 3.4 | 0 | 1.5 | 3.1 |
| K | Comparison example 8 | 34 | 58 | 3.4 | 2.3 | 0 | 2.3 |

2. Methods 2.1 Tail-flick experiment for mice: Healthy male mice weighing 20-24 g were selected and randomly divided into model group, positive drug group and *Ginkgo* diterpene lactone composition groups A-K, with 10 rats in each group. The mice in the positive drug group were orally administered with imipramine tablets in a daily dose of 50 mg/kg, and the mice in the *Ginkgo* diterpene lactone composition groups A-K were administered in a daily dose of 9 mg/kg (ig), once a day for 5 consecutive days. The experiment was started 30 minutes after the fifth administration. In the experiment, a 2 cm portion of the tail of the mouse was affixed to a wooden stick to make the animal upside down, and its head was about 5 cm from the ground. The lines of sight of the animals were blocked with plates on both sides, and the immobility time of the animals in the last 3 minutes of 6 minutes. It was measured once before the administration and once 5 days after the administration. The difference between the two immobility times of the mice themselves were calculated and then statistical analysis was conducted after Ig (X+86) conversion.

2.2 Forced swimming experiment for mice: Male mice weighing 20-24 g were selected, grouped and administered in the same manner as in Section 2.1. The experiment was started 30 minutes after the fifth administration. The mice were placed in a graduated cylinder (20 cm in height and 14 cm in diameter) with 30° C. water in the depth of 10 cm. The difference between the two immobility times of the mice themselves were calculated and then statistical analysis was conducted after Ig (X++45) conversion.

2.3 Electric shock avoidance experiment for rats: The anti-depression effect of the drug was observed using a learned helplessness electric shock model. Healthy male rats weighing 180-220 g were selected and randomly divided into normal group, model group, positive drug group and *Ginkgo* diterpene lactone composition groups A-K, with 10 rats in each group. The rats in the mold drug group were orally administered with the same normal saline every day; the rats in the positive drug group were orally administered with imipramine tablet in a daily dose of 33 mg/kg, and the rats in the *Ginkgo* diterpene lactone composition groups A-K were administered in a daily dose of 6.26 mg/kg (ig), once a day for 35 consecutive days. The experiment was started 30 minutes after the 30th administration. On the first day of the experiment, "helpless induction" was performed. A 20×10×10 cm cage having copper bars at the bottom was used to give the animals 60 random inescapable electric shock in the foot (0.85 mA, 15 s, once every 1 min), rats in the normal group were placed in the same cage but not subjected to the electric shock. 48 hours later, avoidance training was started. A 20×10×10 cm shuttle box with a copper bar spacing of 1 cm at the bottom was used. The animals were individually placed at one end in the shuttle box and allowed to get adapted for 5 min, and then subjected to avoidance training for 20 times at an interval of 30 s. During the training, a light signal is sent first to allow the animals to reach the other end during this period to avoid electric shock. If no response occurs, the light signal will continue for another 3 s, accompanying by a 0.8 mA, 3 s foot shock. If the rats still had no response, the electric shock and light signal were stopped immediately and an escape failure record was made. The training was conducted for 5 days, and the number of successful escapes of each rat during training was recorded every day, and the results of the fifth training were counted.

2.4 Statistical analysis: The data are expressed as ($\bar{x}$±s). All data are analyzed by one-way ANOVA using SPSS 19.0 software to determine the significance of the difference.

3. Results

As can be seen from Table 1, compared with the model group, imipramine significantly prolonged the tail flick interval and swimming interval of mice, and the difference was statistically significant (compared with the normal group, P<0.01). After administration of the *Ginkgo* diterpene lactone composition, the tail flick interval and swimming interval time were prolonged to varying degrees, and the improvement effect of the groups A-C was more obvious (compared with the model group, P<0.01) and was significantly better than that of the groups D-K (Compared with the model group, P<0.05), and the depression state could be improved better.

TABLE 1

Anti-depression effect of the ginkgo diterpene lactone composition on mice ($\overline{X} \pm S$, n = 10)

| Group | Tail flick interval Lg(X + 86) conversion | Swimming interval (X + 45) conversion |
|---|---|---|
| Model group | 1.42 ± 0.14 | 1.55 ± 0.05 |
| Imipramine group | 3.98 ± 0.35## | 4.03 ± 0.05 |
| Group A | 3.89 ± 0.12## | 3.87 ± 0.02## |
| Group B | 3.65 ± 0.32## | 3.55 ± 0.11## |
| Group C | 3.45 ± 0.25## | 3.36 ± 0.08## |
| Group D | 1.86 ± 0.56# | 1.92 ± 0.56# |
| Group E | 2.05 ± 0.25# | 2.15 ± 0.05# |
| Group F | 2.28 ± 0.85# | 2.28 ± 0.06# |
| Group G | 2.35 ± 0.12# | 2.33 ± 0.08# |
| Group H | 2.72 ± 0.23# | 2.46 ± 0.06# |
| Group I | 2.16 ± 0.42# | 1.98 ± 0.04# |
| Group J | 2.33 ± 0.25# | 2.05 ± 0.03# |
| Group K | 2.34 ± 0.52# | 2.08 ± 0.06# |

It can be seen from Table 2 that compared with the normal group, the number of escapes of the rats in the model group from electric shock was significantly reduced (P<0.01). After administration of the positive drug imipramine, compared with the model group, imipramine significantly increased the number of escapes of the rats from electric shock, and the difference was statistically significant (compared with the model group, P<0.01). After administration of the Ginkgo diterpene lactone composition, the number of escapes of the rats from electric shock was significantly increased, and the improvement effect of the groups A-C was more obvious (compared with the model group, P<0.01) and significantly better than that of the groups D-K (compared with the model group, P<0.05), and the depression state could be improved better.

TABLE 2

Anti-depression effect of the ginkgo diterpene lactone composition on rats ($\overline{X} \pm S$, n = 10)

| Group | Accumulative number of successful escapes |
|---|---|
| Normal group | 25.8 ± 1.9 |
| Model group | 13.8 ± 2.1** |
| Imipramine group | 24.5 ± 1.5## |
| Group A | 24.8 ± 1.3## |
| Group B | 23.8 ± 1.8## |
| Group C | 21.5 ± 2.1## |
| Group D | 14.5 ± 2.8# |
| Group E | 19.2 ± 2.2# |
| Group F | 19.6 ± 1.5# |
| Group G | 18.2 ± 2.8# |
| Group H | 20.5 ± 1.6# |
| Group I | 18.6 ± 3.2# |
| Group J | 17.3 ± 2.9# |
| Group K | 18.8 ± 1.6# |

Example 2 Oxidative Stress Resistance Effect of the Ginkgo Diterpene Lactone Composition 1. Materials Animals: SPF male SD rats, weighing 200-220 g, provided by Qinglongshan Animal Breeding Farm, Jiangning District, Nanjing, with a certificate number of SCXK (Jiangsu) 2016-0008.

Test drugs: Each Ginkgo diterpene lactone compound is a commercially available standard product, and the gingko diterpene lactone composition groups A-K with different ratios of components were formulated according to the ratios described in the above table, and then dissolved with 0.5% meglumine and 0.15% citric acid to prepare experimental solutions. The positive drug was edaravone injection (Nanjing Simcere Dongyuan Pharmaceutical Co., Ltd., 30 mg/injection).

Main reagents: 10% chloral hydrate (Beijing Peak Albert Biotechnology Co., Ltd.); malondialdehyde assay kit (MDA), superoxide dismutase test kit (SOD), glutathione test kit (GSH), and total oxidative capacity test kit (TAC) and BCA Protein test kit were all purchased from Nanjing Jiancheng Bioengineering Institute.

Main instruments: MP12001 electronic balance (Shanghai Hengping Scientific Instrument Co., Ltd.), AR2140 electronic analytical balance (Ocesis International Trade (Shanghai) Co., Ltd.), DHG-9053A electric thermostatic drying oven (Shanghai Medical Thermostatic Equipment Factory), and Enspire multifunctional microplate reader (PerkinElmer Instruments Co., Ltd.), 5804R low-temperature high-speed centrifuge (Eppendorf China Co., Ltd.).

2. Methods 2.1 Modeling and administration: Healthy male rats were selected and randomly divided into normal group, model group, positive drug group and Ginkgo diterpene lactone composition groups A-K, With the exception of the normal group, the other groups were orally administered with alcohol with a daily dose of 6 g/kg. Rats in the positive drug group were administrated with edaravone injection (iv) in a daily dose of 6.25 mg/kg, and rats in the Ginkgo diterpene lactone composition groups A-K were administrated in a daily dose of 3 mg/kg (iv), they were continuously administrated or given alcohol for 5 weeks.

2.2 Detection of oxidative stress: After the administration, rats in each group were anesthetized with 10% chloral hydrate, abdominal aortic blood was collected and then subjected to heparin anticoagulation to separate serum; changes of MDA, SOD, GSH and TAC levels in the serum were detected according to the instructions of the kits, and the protein content of each sample was measured using the BCA protein test kit.

2.3 Statistical analysis: The data are expressed as ($\overline{x} \pm s$). All data are analyzed by one-way ANOVA using SPSS 19.0 software to determine the significance of the difference.

3. Results

As can be seen from Table 3, compared with the normal group, the MDA level in the model group increased significantly (P<0.01), while the SOD, GSH, and TAC levels decreased significantly (compared with the normal group, P<0.01), indicating that the rats have suffered significant oxidative damage. After the administration of the edaravone injection, all indicators were significantly corrected (compared with the model group, P<0.01). After the administration of the Ginkgo diterpene lactone composition, SOD, MDA, GSH, TAC and other indicators were improved to varying degrees, and the improvement effect of the groups A-C was more obvious (compared with the model group, P<0.01), and significantly better than the groups D-K (compared with the model group, P<0.05); the level of oxidative stress and the oxidative damage could be better ameliorated.

TABLE 3

Effect of the ginkgo diterpene lactone composition on level of oxidative stress of rats (n = 10)

| Group | SOD (U/mg) | GSH (mg/mg) | MDA (nmol/mg) | TAC (U/mg) |
|---|---|---|---|---|
| Normal group | 935.8 ± 52.9 | 79.8 ± 20.1 | 57.3 ± 17.1 | 261.9 ± 06 |
| Model group | 363.8 ± 121.1** | 38.1 ± 15.1** | 116.5 ± 24.3** | 55.9 ± 1.5** |
| Edaravone group | 769.5 ± 55.5## | 62.3 ± 6.8## | 59.6 ± 20.6## | 243.6 ± 0.9## |
| Group A | 725.8 ± 54.5## | 69.8 ± 10.0## | 60.9 ± 20.4## | 255.0 ± 1.5## |
| Group B | 745.8 ± 56.8## | 66.2 ± 6.8## | 65.8 ± 25.5## | 250.2 ± 0.6## |
| Group C | 765.5 ± 45.8## | 62.8 ± 5.2## | 69.8 ± 18.5## | 243.8 ± 2.1## |
| Group D | 458.5 ± 56.8# | 45.8 ± 5.2# | 89.5 ± 15.8# | 77.2 ± 0.6# |
| Group E | 456.2 ± 56.2# | 49.9 ± 8.5# | 81.5 ± 16.5# | 81.8 ± 1.7# |
| Group F | 487.6 ± 49.5# | 50.5 ± 10.5# | 78.5 ± 15.6# | 86.0 ± 1.4# |
| Group G | 546.2 ± 65.8# | 53.8 ± 12.5# | 79.5 ± 12.5# | 96.6 ± 0.8# |
| Group H | 623.5 ± 75.6# | 58.9 ± 15.3# | 73.9 ± 15.3# | 126.2 ± 0.6# |
| Group I | 598.6 ± 65.2# | 53.5 ± 12.5# | 75.8 ± 21.5# | 105.8 ± 1.0# |
| Group J | 505.3 ± 56.9# | 56.4 ± 8.9# | 78.5 ± 20.5# | 96.5 ± 0.8# |
| Group K | 546.8 ± 75.6# | 55.3 ± 7.8# | 77.6 ± 18.6# | 105.3 ± 1.2# |

The above are only the preferred embodiments of the present invention. It should be noted that, for those with ordinary skill in the art, without departing from the principles of the present invention, several improvements and retouches can be made and these improvements and retouches should also be regarded as falling within the scope off the present invention.

What is claimed is:

1. A *Ginkgo* diterpene lactone composition consisting of, by weight: 32.9-34.1% of GA, 56.1-57.9% of GB, 2.4-3.4% of GK, and GC, GJ and GL in the total content of 4.6-8%.

2. The composition according to claim 1, wherein the content of GC accounts for 3.2-3.8% by weight, the content of GJ accounts for 0.5-3.5% by weight, and the content of GL accounts for 0.5-1.4% by weight in the composition.

3. A *Ginkgo* diterpene lactone preparation containing the composition according to claim 2, wherein the preparation further comprises pharmaceutically acceptable excipients.

4. A *Ginkgo* diterpene lactone preparation containing the composition according to claim 1, wherein the preparation further comprises pharmaceutically acceptable excipients.

5. A *Ginkgo* diterpene lactone injection containing the composition according to claim 1.

6. The injection according to claim 5, wherein the injection is in a dose of 1 ml or 5 ml or 10 ml, containing 5±0.5 mg or 25±0.5 mg or 50±0.5 mg of the *Ginkgo* diterpene lactone composition respectively.

7. The injection according to claim 5, further containing meglumine and sodium chloride, wherein the weight ratio of the *Ginkgo* diterpene lactone composition to meglumine to sodium chloride is (2-8): (2-8): (4-12).

8. The application of the composition according to claim 1 in the preparation of an antidepressant drug.

9. The application of the composition according to claim 1 in the preparation of a drug for treating cardiovascular and cerebrovascular diseases.

10. The application of the composition according to claim 1 in the preparation of a drug for ameliorating oxidative stress.

* * * * *